(12) United States Patent
Day et al.

(10) Patent No.: US 6,756,401 B2
(45) Date of Patent: Jun. 29, 2004

(54) COMPOSITIONS AND METHODS FOR TREATING OSTEOPOROSIS AND LOWERING CHOLESTEROL

(75) Inventors: Wesley W. Day, Old Lyme, CT (US); Andrew G. Lee, Old Lyme, CT (US); David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/767,625

(22) Filed: Jan. 23, 2001

(65) Prior Publication Data

US 2003/0162807 A1 Aug. 28, 2003

Related U.S. Application Data

(60) Provisional application No. 60/205,327, filed on Apr. 21, 2000, and provisional application No. 60/188,923, filed on Jan. 26, 2000.

(51) Int. Cl.$^7$ .................... A61K 31/40; A61K 31/34
(52) U.S. Cl. .................... 514/428; 514/461; 514/473
(58) Field of Search .................... 514/317, 331, 514/428, 213, 423

(56) References Cited

U.S. PATENT DOCUMENTS

| | | | |
|---|---|---|---|
| 5,543,542 A | * | 8/1996 | Lawrence et al. ............. 558/87 |
| 5,552,412 A | | 9/1996 | Cameron et al. |
| 5,948,809 A | | 9/1999 | Chiu et al. |
| 6,022,887 A | | 2/2000 | Gasper et al. |
| 6,080,779 A | | 6/2000 | Gasper et al. |
| 6,107,331 A | | 8/2000 | MacLean et al. |
| 6,204,286 B1 | | 3/2001 | Cameron et al. |

FOREIGN PATENT DOCUMENTS

| | | | |
|---|---|---|---|
| EP | 0459632 | 12/1991 | ........... C08F/20/60 |
| EP | 0888775 | 1/1999 | ......... A61K/31/565 |
| WO | WO 9731640 | 9/1997 | ......... A61K/31/557 |
| WO | WO9818775 | 5/1998 | |
| WO | WO9945923 | 9/1999 | |

OTHER PUBLICATIONS

Gradishar, W.J. et al., *Journal of Clinical Oncology* (1997), Feb., vol. 15, No. 2, 840–852, *Clinical Potential of New Antiestrogens*.

Draper, M.W. et al., *Journal of Bone and Mineral Research* (1996), vol. 11, No. 6, 835–842, *A Controlled Trial of Raloxifene (LY139481) HCI: Impact of Bone Turnover and Serum Lipid Profile in Healthy Postmenopausal Women*.

Walsh, B.W. et al., *JAMA* (1998), May 13, vol. 279, No. 18, Raloxifene in Postmenopausal Women, 1445–1451, *Effects of Raloxifene on Serum Lipids and Coagulation Factors in Healthy Postmenopausal Women*.

Jordan, V.C., *Scientific American* (1998) Oct. 60–67, *Designer Estrogens—These compounds–also called SERM-s–have evolved from mere laboratory curiosities into drugs that hold promise for preventing several major disorders in women*.

G. Mundy, et al., *Sciene*, "Stimulation of Bone Formation in Vitro and in Rodents by Statins", vol. 286, pp. 1946–1949, (Dec. 3, 1999).

\* cited by examiner

Primary Examiner—Theodore J. Criares
(74) Attorney, Agent, or Firm—Peter C. Richardson; Gregg C. Benson; John A. Wichtowski (57) ABSTRACT

This invention relates to methods, pharmaceutical compositions and kits useful in promoting bone formation and/or preventing bone loss and lowering blood cholesterol. The compositions are comprised of an estrogen agonist/antagonist as a first active component and a statin as a second active component and a pharmaceutically acceptable vehicle, carrier or diluent. The compositions and methods of treatment are effective while substantially reducing the concomitant liability of adverse effects associated with estrogen administration.

6 Claims, 1 Drawing Sheet

FIG. 1

COMPOSITIONS AND METHODS FOR TREATING OSTEOPOROSIS AND LOWERING CHOLESTEROL

CROSS REFERENCE TO RELATED APPLICATION

This application claims priority from U.S. provisional application No. 60/188,923, filed Jan. 26, 2000 and No. 60/205,327, filed Apr. 21, 2000.

FIELD OF THE INVENTION

This invention relates to pharmaceutical compositions containing combinations of estrogen agonists/antagonists and statins, and pharmaceutically acceptable salts thereof, kits containing such combinations and methods of using such combinations to prevent bone loss and/or promote bone formation and to lower blood lipid levels. The compositions and methods are useful for treating subjects suffering from osteoporosis, bone fracture or deficiency, primary or secondary hyparathyroidism, periodontal disease, metastatic bone disease, osteolytic bone disease, or undergoing orthopedic or oral surgery and treating cardiovascular disease, atherosclerosis and hyperlipidemia, or presenting with symptoms of cardiac risk.

BACKGROUND OF THE INVENTION

Estrogen alters serum lipid concentrations, coagulation and fibrinolytic systems, antioxidant systems, and the production of other vasoactive molecules, such as nitric oxide and prostaglandins, all of which can influence the development of vascular disease.

The effects of estrogen therapy on serum lipid concentrations may result largely from estrogen-receptor-mediated effects on the hepatic expression of apoprotein genes. Many studies, including one large, randomized, controlled trial (The Writing Group for the PEPI Trial, *JAMA* 1995;273:199–208. [Erratum, JAMA 1995;274:1676.]) have documented that estrogen therapy in post-menopausal women decreases serum total cholesterol and low density lipoprotein (LDL) cholesterol concentrations, increases serum high-density lipoprotein (HDL) cholesterol and triglyceride concentrations, and decreases serum Lp(a) lipoprotein concentrations. Hepatic expression of the genes for several coagulation and fibrinolytic proteins is also regulated by estrogen through estrogen receptors.

Statins inhibit the enzyme HMG-CoA reductase that catalyzes the conversion of 3-hydroxy-3-methylglutaryl-coenzyme A (HMG-CoA) to mevalonate in an early and rate-limiting step in the cholesterol biosynthetic pathway. It is believed that this effect is responsible for statins being considered as potent lipid lowering agents. The bone-forming effect of statins may be due to their ability to increase bone formation rate possibly through the stimulation of growth factors such as bone morphogenic protein-2 (BMP-2) (Mundy, G., et al., *Science*, 1999;286:1946–1949).

Statins include such compounds as simvastatin, disclosed in U.S. Pat. No. 4,444,784; pravastatin, disclosed in U.S. Pat. No. 4,346,227; cerivastatin, disclosed in U.S. Pat. No. 5,502,199; mevastatin, disclosed in U.S. Pat. No. 3,983,140; velostatin, disclosed in U.S. Pat. Nos. 4,448,784 and 4,450,171; fluvastatin, disclosed in U.S. Pat. No. 4,739,073; compactin, disclosed in U.S. Pat. No. 4,804,770; lovastatin, disclosed in U.S. Pat. No. 4,231,938; dalvastatin, disclosed in European Patent Application Publication No. 738510 A2; fluindostatin, disclosed in European Patent Application Publication No. 363934 A1; atorvastatin, disclosed in U.S. Pat. No. 4,681,893; atorvastatin calcium, disclosed in U.S. Pat. No. 5,273,995; dihydrocompactin, disclosed in U.S. Pat. No. 4,450,171; ZD-4522, disclosed in U.S. Pat. No. 5,260,440; bervastatin, disclosed in U.S. Pat. No. 5,082,859; and NK-104, disclosed in U.S. Pat. No. 5,102,888.

High levels of blood cholesterol and blood lipids are conditions involved in the onset of atherosclerosis. It is well known that inhibitors of 3-hydroxy-3-methylglutaryl-coenzyme A reductase (HMG-CoA reductase) are effective in lowering the level of blood plasma cholesterol, especially low density lipoprotein cholesterol (LDL-C), in man (Brown and Goldstein, *N Engl J Med*, 1981;305:515–517). It has now been established that lowering LDL-C levels affords protection from coronary heart disease (see, e.g., The Scandinavian Simvastatin Survival Study Group: Randomised trial of cholesterol lowering in 4444 patients with coronary heart disease: the Scandinavian Simvastatin Survival Study (4S), *Lancet*, 1994;344:1383–89; and Shepherd, J. et al., Prevention of coronary heart disease with pravastatin in men with hypercholesterolemia, *N Engl J Med*, 1995;333:1301–07).

Coronary heart disease is a multifactorial disease in which the incidence and severity are affected by the lipid profile, the presence of diabetes and the sex of the subject. Incidence is also affected by smoking and left ventricular hypertrophy, which is secondary to hypertension. To meaningfully reduce the risk of coronary heart disease, it is important to manage the entire risk spectrum. For example, hypertension intervention trials have failed to demonstrate full normalization in cardiovascular mortality due to coronary heart disease. Treatment with cholesterol synthesis inhibitors in patients with and without coronary artery disease reduces the incidence of cardiovascular morbidity and the risk of mortality.

The incidence of cardiovascular disease differs significantly between men and women, in part because of differences in risk factors and hormones (Barrett-Connor E. *Circulation* 1997;95:252–64). The incidence of atherosclerotic diseases is low in premenopausal women, rises in post-menopausal women, and is reduced to premenopausal levels in post-menopausal women who receive estrogen therapy. (Barrett-Connor E., *Circulation* 1997;95:252–64; Stampfer M. J., et al., *N Enql J Med* 1991;325:756–62.; Grady D., et al., *Ann Intern Med* 1992;117:1016–37) Until recently, the atheroprotective effects of estrogen were attributed principally to the hormone's effects on serum lipid concentrations. However, estrogen-induced alterations in serum lipids account for only approximately one third of the observed clinical benefits of estrogen (Grady D., et al., *Ann Intern Med* 1992;117:1016–37; Mendelsohn M. E., Karas R. H. *Curr Opin Cardiol* 1994;9:619–26; Bush T. L., et al., *Circulation* 1987;75:1102–9). The results, however, can be nonetheless significant. It is now also believed that the direct actions of estrogen on blood vessels contribute substantially to the cardiovascular protective effects of estrogen (Mendelsohn M. E., *Curr Opin Cardiol* 1994;9:619–26; Farhat M. Y. et al., *FASEB J* 1996;10:615–24).

The hormone estrogen has a profound effect in the vascular system of both men and women although its administration is associated with other effects that can be undesirable. Estrogen increases vasodilatation and inhibits the response of blood vessels to injury and the development of atherosclerosis. Estrogen-induced vasodilatation occurs 5 to 20 minutes after estrogen has been administered and is not dependent on changes in gene expression; this action of estrogen is sometimes referred to as "nongenomic." The estrogen-induced inhibition of the response to vascular injury and the preventive effect of estrogen against atherosclerosis occur over a period of hours or days after estrogen treatment and are dependent on changes in gene expression in the vascular tissues; these actions are sometimes referred to as "genomic."

There are two estrogen receptors, estrogen receptor α and estrogen receptor β, both of which are members of the superfamily of steroid hormone receptors. (Walter P., et al., *Proc Nad Acad Sci USA* 1985;82:7889–93; Kuiper G. G. J. M., et al; *Proc Nad Acad Sci USA* 1996;93:5925–30) Estrogen receptors α and β have considerable homology and, like all steroid hormone receptors, are transcription factors that alter gene expression when they are activated. (Walter P., et al. *Proc Nad Acad Sci USA* 1985;82:7889–93; Kuiper G. G. J. M., et al.; *Proc Nad Acad Sci USA* 1996;93:5925–30; Shibata H., et al. *Recent Prog Horm Res* 1997;52:141–65; Evans R. M., *Science* 1988;240:889–95; Brown M., *Hematol Oncol Clin North Am* 1994;8:101–12). Blood vessels are complex structures, with walls containing smooth-muscle cells and an endothelial cell lining. Vascular endothelial and smooth muscle cells bind estrogen with high affinity (Mendelsohn M. E., et al., *Curr Opin Cardiol* 1994;9:619–26; Farhat M. Y., et al., *FASEB J* 1996;10:615–24) and estrogen receptor α has been identified in both types of vascular cells in women and men, (Karas R. H., et al., *Circulation* 1994;89:1943–50; Losordo D. W., et al., *Circulation* 1994;89:1501–10; Venkov C. D., et al., *Circulation* 1996;94:727–33; Kim-Schulze S., et al., *Circulation* 1996;94:1402–7; Caulin-Glaser T., et al., *J Clin Invest* 1996;98:36–42) as well as in myocardial cells (Grohe C., et al., *FEBS Lett* 1997;416:107–12).

Estrogen receptor a activates specific target genes in vascular smooth-muscle and endothelial cells (Karas R. H., et al., *Circulation* 1994;89:1943–50, Venkov C. D., et al., *Circulation* 1996;94:727–33; Kim-Schulze S., et al., *Circulation* 1996;94:1402–7; Caulin-Glaser T., et al., *J Clin Invest* 1996;98:36–42; Koike H., et al., *J Vasc Surg* 1996;23:477–82). Estrogen receptor β is structurally and functionally distinct from estrogen receptor α. Functional estrogen receptor β is also present in myocardial cells, in which it regulates the expression of nitric oxide synthases.

Bone is a tissue that is subject to turnover. The osteoblasts that produce new bone and the osteoclasts that destroy bone balance bone homeostasis. The activities of these cells are regulated by a large number of cytokines and growth factors, many of which have now been identified and cloned. Mundy has described the current knowledge related to these factors (Mundy, G. R., *Clin Orthop* 1996;324:24–28; Mundy, G. R., *J Bone Miner Res* 1993;8:S505–10.

Growth factors that stimulate bone formation have been identified. Among these latter factors are transforming growth factor, the heparin-binding growth factors (acidic and basic fibroblast growth factor), the insulin-like growth factors (insulin-like growth factor I and insulin-like growth factor II), and a recently described family of proteins called bone morphogenetic proteins (BMPs). All of these growth factors have effects on other types of cells, as well as on bone cells. The BMPs are novel factors in the extended transforming growth factors β superfamily. The BMPs were identified by Wozney J., et al. *Science* 1988;242: 1528–34, following earlier descriptions characterizing the biological activity in extracts of demineralized bone (Urist M., *Science* 1965;150: 893–99). Recombinant BMP2 and BMP4 can induce new bone formation when they are injected locally into the subcutaneous tissues of rats (Wozney J., *Molec Reprod Dev* 1992;32:160–67). These factors are expressed by normal osteoblasts as they differentiate, and have been shown to stimulate osteoblast differentiation and bone nodule formation in vitro as well as bone formation in vivo (Harris S., et al. *J. Bone Miner Res* 1994;9:855–63).

As osteoblasts differentiate from precursors to mature bone-forming cells, they express and secrete a number of enzymes and structural proteins of the bone matrix, including Type-1 collagen, osteocalcin, osteopontin and alkaline phosphatase (Stein G., et al. *Curr Opin Cell Biol* 1990;2:1018–27; Harris S., et al. (1994), supra). They also synthesize a number of growth regulatory peptides, which are stored in the bone matrix, and are presumably responsible for normal bone formation. These growth regulatory peptides include the BMPs (Harris S., et al. (1994), supra). In studies of primary cultures of fetal rat calvarial osteoblasts, BMPs 1, 2, 3, 4, and 6 are expressed by cultured cells prior to the formation of mineralized bone nodules (Harris S., et al. (1994), supra). Like alkaline phosphatase, osteocalcin and osteopontin, the BMPs are expressed by cultured osteoblasts as they proliferate and differentiate.

In premenopausal women, 17β-estradiol produced by the ovaries is the chief circulating estrogen. Serum estradiol concentrations are low in preadolescent girls and increase at menarche. In women, they range from about 100 pg per milliliter (367 pmol per liter) in the follicular phase to about 600 pg per milliliter (2200 pmol per liter) at the time of ovulation. They may rise to nearly 20,000 pg per milliliter (70,000 pmol per liter) during pregnancy. After menopause, serum estradiol concentrations fall to values similar to or lower than those in men of similar age (5 to 20 pg per milliliter [18 to 74 pmol per liter]) (Yen, S. S. C. and Jaffe, R. B. eds. *Reproductive Endocrinology: Physiology, Pathophysiology and Clinical Management*, 3rd ed. Philadelphia: W. B. Saunders, 1991).

Breast cancer is a hormone-dependent disease. Women without functioning ovaries who never receive estrogen replacement do not develop breast cancer. The female-to-male ratio for the disease is about 150 to 1. A host of findings indicate that hormones play a critical role as promoters of the disease. For most epithelial malignancies, a log-log plot of incidence versus age shows a straight-line increase with every year of life. A similar plot for breast cancer shows the same straight-line increase, but with a decrease in slope beginning at the age of menopause. The three dates in a woman's life that have a major impact on breast cancer incidence are age of menarche, age at first full-term pregnancy, and age of menopause. Women who experience menarche at age 16 have only 50 to 60 percent of the lifetime breast cancer risk of women who experience menarche at age 12. Similarly, menopause occurring 10 years before the median age (52 years), whether natural or surgically induced, reduces lifetime breast cancer risk by about 35 percent. Compared with nulliparous women, women who have a first full-term pregnancy by age 18 have 30 to 40 percent the risk of breast cancer. Thus, length of menstrual life—particularly the fraction occurring before the first full-term pregnancy—is a substantial component of the total risk of breast cancer. This factor can account for 70 to 80 percent of the variation in breast cancer frequency in different countries.

International variation has provided some of the most important clues on hormonal carcinogenesis. A woman living to age 80 in North America has 1 chance in 9 of developing invasive breast cancer. Asian women have one-fifth to one-tenth the risk of breast cancer of women in North America or Western Europe. Asian women have substantially lower concentrations of estrogens and progesterone. These differences cannot be explained on a genetic basis, because Asian women living in a Western environment have a risk identical to that of their Western counterparts. These women also differ markedly in height and weight from Asian women in Asia; height and weight are critical regulators of age of menarche and have substantial effects on plasma concentrations of estrogens. (Lippman, M. E., *Breast Cancer*, Chapter 91, in *Harrison's Principles of Internal Medicine*, 14th ed., 1998). Thus despite the beneficial effects which estrogens play in maintaining health, the administration of estrogens may also cause adverse effects on a subject's health such as an increased risk of breast cancer breast cancer.

Menopause occurs naturally at an average age of 50 to 51 years in the USA. As ovaries age, response to pituitary gonadotropins (follicle-stimulating hormone [FSH] and luteinizing hormone [LH]) decreases, initially resulting in shorter follicular phases (thus, shorter menstrual cycles), fewer ovulations, decreased progesterone production, and more irregularity in cycles. Eventually, the follicle fails to respond and does not produce estrogen. The transitional phase, during which a woman passes out of the reproductive stage, begins before menopause. It is termed the climacteric or perimenopause, although many persons refer to it as menopause.

Premature menopause refers to ovarian failure of unknown cause that occurs before age 40. It may be associated with smoking, living at high altitude, or poor nutritional status. Artificial menopause may result from oophorectomy, chemotherapy, radiation of the pelvis, or any process that impairs ovarian blood supply.

The compositions and methods of the present invention act to promote bone formation, lower blood cholesterol and treat hyperlipidemia. These effects are accomplished by the compositions and methods of the invention with a substantial reduction of the concomitant liability of adverse effects associated with estrogen administration. Not being bound by any single theory, it is believed that administration of the estrogen agonist/antagonist of the invention results in a bone loss preventing effect and a lipid lowering effect distinct from that of statins. The combined overall effect of combined treatment with estrogen agonists/antagonists and statins is a beneficial one and is substantially free of the adverse effects attributed to estrogen administration.

SUMMARY OF THE INVENTION

This invention relates to pharmaceutical compositions useful for promoting bone formation and/or preventing bone loss and lowering blood cholesterol. The compositions are comprised of an estrogen agonist/antagonist and a statin and a pharmaceutically acceptable carrier, vehicle or diluent. The compositions exert an effect which is additive or greater than the sum of the individual effects of the estrogen agonists/antagonists and statins when administered separately.

A second aspect of the invention relates to methods of promoting bone formation and/or preventing bone loss and lowering blood cholesterol. The methods comprise the administration of an effective amount of the pharmaceutical compositions as described herein or co-administration of the active components of the compositions.

A third aspect of the invention is that the compositions for and methods of promoting bone formation and/or preventing bone loss and lowering blood cholesterol while substantially reducing the concomitant liability of adverse effects associated with estrogen administration.

As a fourth aspect, the present invention provides for kits for use by a consumer to promote bone formation and/or prevent bone loss and lower blood cholesterol. The kits comprise: a) a pharmaceutical composition comprising an estrogen agonist/antagonist and a pharmaceutically acceptable carrier, vehicle or diluent; b) a pharmaceutical composition comprising a statin and a pharmaceutically acceptable carrier, vehicle or diluent; and, optionally, c) instructions describing a method of using the pharmaceutical compositions for promoting bone formation and/or preventing bone loss and lowering blood cholesterol or another specific condition related to these effects. The instructions may also indicate that the kit is for promoting bone formation and/or preventing bone loss and lowering blood cholesterol or another specific condition related to these effects while substantially reducing the concomitant liability of adverse effects associated with estrogen administration. The estrogen agonist/antagonist and the statin contained in the kit may be optionally combined in the same pharmaceutical composition.

As a fifth aspect, the present invention provides for the use of estrogen agonists/antagonists of the present invention and statins for the manufacture of a medicament to promote bone formation and/or prevent bone loss and/or lower blood cholesterol. These indications are also treated by the medicament while substantially reducing the concomitant liability of adverse effects associated with estrogen administration.

DETAILED DESCRIPTION OF THE INVENTION

The present invention relates to compositions and methods for promoting bone formation and/or preventing bone loss and lowering blood cholesterol and treating hyperlipidemia. Unless otherwise specified, the following terms have the meanings as defined below:

As used herein, "limit" and "treat" are interchangeable terms as are "limiting" and "treating" and, as used herein, include preventative (e.g., prophylactic) and palliative treatment or the act of providing preventative or palliative treatment. The terms include a postponement of development of bone deficit symptoms and/or a reduction in the severity of such symptoms that will or are expected to develop. The terms further include ameliorating existing bone or cartilage deficits, preventing additional deficits, ameliorating or preventing the underlying metabolic causes of such deficits, preventing or reversing bone resorption and/or encouraging bone growth. Thus, the terms denote that a beneficial result has been conferred on a vertebrate subject with a cartilage, bone or skeletal deficit, or with the potential to develop such deficit. By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired. The terms further include the lowering of existing blood cholesterol levels and the prevention of the elevation of blood cholesterol levels and the symptoms and conditions caused or related to the blood cholesterol levels such as atherosclerosis and hyperlipidemia, or increased cardiac risk.

Representative uses of the compositions and methods of the present invention include: repair of bone defects and deficiencies, such as those occurring in closed, open and nonunion fractures; prophylactic use in closed and open fracture reduction; promotion of bone healing in plastic surgery; stimulation of bone ingrowth into non-cemented prosthetic joints and dental implants; elevation of peak bone mass in perimenopausal women, treatment of growth deficiencies; treatment of periodontal disease and defects, and other tooth repair processes; increase in bone formation during distraction osteogenesis; and treatment of other skeletal disorders, such as age-related osteoporosis in females or males, post-menopausal osteoporosis, glucocorticoid-induced osteoporosis or disuse osteoporosis and arthritis, or any condition that benefits from stimulation of bone formation. The compositions and methods of the present invention can also be useful in repair of congenital, trauma-induced or surgical resection of bone (for instance, for cancer treatment), and in cosmetic surgery. Further, the compositions and methods of the present invention can be used for treating cartilage defects or disorders, and are useful in wound healing or tissue repair.

Bone or cartilage deficit or defect can be treated in vertebrate subjects by administering the compositions of the invention. The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compositions disclosed herein may be administered in a cyclical manner (administration of disclosed compound, followed by no administration, followed by administration of disclosed compositions, and the like). Treatment will continue until the desired outcome is achieved.

A "subject" is an animal including a human that is treatable with the compositions, methods and kits of the present invention. The term "subject" or "subjects" is intended to refer to both the male and female gender unless one gender is specifically indicated.

"Adverse effects associated with estrogen" include breast tenderness, bloating, headache, increased blood clotting and menstrual bleeding in women. Unopposed estrogen therapy increases the risk of endometrial carcinoma. Women on long-term estrogen therapy may have an increased risk that is not reversed by concurrent progestin (*N Engl J Med* 1995;332:1589). In men, the adverse effects of estrogen include increased blood clotting, gynecomastia, feminization and decreased libido.

The term "post-menopausal women" is defined to include not only women of advanced age who have passed through menopause, but also women who have been hysterectomized or for some other reason have suppressed estrogen production, such as those who have undergone long-term administration of corticosteroids, suffer from Cushions' syndrome or have gonadal dysgenesis.

"Breast cancer" is defined as a malignant proliferation of epithelial cells lining the ducts or lobules of the breast.

"Co-administration" of a combination of a estrogen agonist/antagonist and a statin means that these components can be administered together as a composition or as part of the same, unitary dosage form. "Co-administration" also includes administering an estrogen agonist/antagonist and a statin separately but as part of the same therapeutic treatment program or regimen. The components need not necessarily be administered at essentially the same time, although they can if so desired. Thus "co-administration" includes, for example, administering a estrogen agonist/antagonist and a statin as separate dosages or dosage forms, but at the same time. "Co-administration" also includes separate administration at different times and in any order. For example, where appropriate a patient may take one or more component(s) of the treatment in the morning and the one or more of the other component(s) at night.

An "estrogen agonist/antagonist" is a compound that affects some of the same receptors that estrogen does, but not all, and in some instances, it antagonizes or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark, et al., *Steroids* 1973;22:707, Capony et al., *Mol Cell Endocrinol*, 1975;3:233).

An estrogen agonist/antagonist and statin when co-administered either as part of the same pharmaceutical composition or as separate pharmaceutical compositions is/are effective in promoting bone formation and/or preventing bone loss and in reducing blood cholesterol. By producing these effects, the compositions and methods of the invention are suitable for treating a variety of conditions. These conditions include osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. The results of the methods in enhancing bone formation make the compositions and methods useful for bone repair and bone deficit conditions. Such conditions would include bone fracture and facial reconstruction surgery and bone segmental defects, periodontal disease, metastatic bone disease, osteolytic bone disease and conditions where connective tissue repair would be beneficial, such as healing or regeneration of cartilage defects or injury. Such compositions and methods also are useful for treating subjects with cardiovascular disease, atherosclerosis and hyperlipidemia, or those subjects presenting with symptoms of cardiac risk.

Preferred estrogen agonists/antagonists of the present invention include the compounds described in U.S. Pat. No. 5,552,412. Those compounds are described by formula (I) given below:

(I)

wherein:
A is selected from CH$_2$ and NR;
B, D and E are independently selected from CH and N;
Y is
  (a) phenyl, optionally substituted with 1–3 substituents independently selected from R$^4$;
  (b) naphthyl, optionally substituted with 1–3 substituents independently selected from R$^4$;
  (c) C$_3$–C$_8$ cycloalkyl, optionally substituted with 1–2 substituents independently selected from R$^4$;
  (d) C$_3$–C$_8$ cycloalkenyl, optionally substituted with 1–2 substituents independently selected from R$^4$;
  (e) a five membered heterocycle containing up to two heteroatoms selected from the group consisting of —O—, —NR$^2$— and —S(O)$_n$—, optionally substituted with 1–3 substituents independently selected from R$^4$;
  (f) a six membered heterocycle containing up to two heteroatoms selected from the group consisting of —O—, —NR$^2$— and —S(O)$_n$— optionally substituted with 1–3 substituents independently selected from R$^4$; or
  (g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;
Z$^1$ is
  (a) —(CH$_2$)$_p$W(CH$_2$)$_q$—;
  (b) —O(CH$_2$)$_p$CR$^5$R$^6$—;
  (c) —O(CH$_2$)$_p$W(CH$_2$)$_q$—;
  (d) —OCHR$^2$CHR$^3$—; or
  (e) —SCHR$^2$CHR$^3$—;
G is
    (a) —NR$^7$R$^8$;
    (b)

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or
    (c) a bicyclic amine containing five to twelve carbon atoms, either bridged or fused and optionally substituted with 1–3 substituents independently selected from R$^4$; or Z$^1$ and G in combination may be W is
  (a) —CH$_2$—;
  (b) —CH=CH—;
  (c) —O—;
  (d) —NR$^2$—;
  (e) —S(O)$_n$—;
  (f)

;

(g) —CR$^2$(OH)—;
  (h) —CONR$^2$—;
  (i) —NR$^2$CO—;

; or

(j)
  (k) —C≡C—;
R is hydrogen or C$_1$–C$_6$ alkyl;
R$^2$ and R$^3$ are independently
  (a) hydrogen; or
  (b) C$_1$–C$_4$ alkyl;
R$^4$ is
  (a) hydrogen;
  (b) halogen;
  (c) C$_1$–C$_6$ alkyl;
  (d) C$_1$–C$_4$ alkoxy;
  (e) C$_1$–C$_4$ acyloxy;
  (f) C$_1$–C$_4$ alkylthio;
  (g) C$_1$–C$_4$ alkylsulfinyl;
  (h) C$_1$–C$_4$ alkylsulfonyl;
  (i) hydroxy (C$_1$–C$_4$)alkyl;
  (j) aryl (C$_1$–C$_4$)alkyl;
  (k) —CO$_2$H;
  (l) —CN;
  (m) —CONHOR;
  (n) —SO$_2$NHR;
  (o) —NH$_2$;
  (p) C$_1$–C$_4$ alkylamino;
  (q) C$_1$–C$_4$ dialkylamino;
  (r) —NHSO$_2$R;
  (s) —NO$_2$;
  (t) -aryl; or
  (u) —OH;
R$^5$ and R$^6$ are independently C$_1$–C$_8$ alkyl or together form a C$_3$–C$_{10}$ carbocyclic ring;
R$^7$ and R$^8$ are independently
  (a) phenyl;
  (b) a C$_3$–C$_{10}$ carbocyclic ring, saturated or unsaturated;
  (c) a C$_3$–C$_{10}$ heterocyclic ring containing up to two heteroatoms, selected from —O—, —N— and —S—;
  (d) H;

(e) $C_1$–$C_6$ alkyl; or
(f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and non-toxic pharmacologically acceptable acid addition salts, N-oxides, esters, quaternary ammonium salts and prodrugs thereof.

By halo is meant chloro, bromo, iodo, or fluoro or by halogen is meant chlorine, bromine, iodine or fluorine.

By alkyl is meant straight chain or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The parenthetical negative or positive sign used herein in the nomenclature denotes the direction plane polarized light is rotated by the particular stereoisomer.

Additional preferred compounds of the invention also disclosed in U.S. Pat. No. 5,552,412 are of the formula (IA):

(IA)

wherein G is $R^4$ is H, OH, F, or Cl; and B and E are independently selected from CH and N.

Especially preferred compounds for the compositions and methods of the invention are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolidinoethoxy-3'-pyridyl]-2-phenyl-6-hydroxy-1,2,3,4-tetrahydronaphthalene;

1-(4'-pyrrolidinoethoxyphenyl)-2-(4"-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol; and 1-(4'-pyrrolidinoethoxyphenyl)-2-phenyl-6-hydroxy-1,2,3,4-tetrahydroisoquinoline and pharmaceutically acceptable salts thereof. An especially preferred salt of (−)-cis-6-phenyl-5-[4-(2-pyrrolidin-1-yl-ethoxy)-phenyl]-5,6,7,8-tetrahydro-naphthalene-2-ol is the tartrate salt.

Other preferred estrogen agonists/antagonists are disclosed in U.S. Pat. No. 5,047,431. The structure of these compounds is given by formula (II) below:

(II)

wherein $R^{1A}$ and $R^{2A}$ may be the same or different and are either H, methyl, ethyl or a benzyl group; and optical or geometric isomers thereof; and pharmaceutically acceptable salts, N-oxides, esters, quaternary ammonium salts, and prodrugs thereof.

Additional preferred estrogen agonists/antagonists are tamoxifen: (ethanamine,2-[-4-(1,2-diphenyl-1-butenyl)phenoxy]-N,N-dimethyl, (Z)-2-, 2-hydroxy-1,2,3-propanetricarboxylate(1:1)) and other compounds as disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl)ethoxy]phenyl]-, hydrochloride) and other compounds as disclosed in U.S. Pat. Nos. 4,418,068; 5,393,763; 5,457,117; 5,478,847 and 5,641,790; toremifene: (ethanamine, 2-[4-(4-chloro-1,2-diphenyl-1-butenyl)phenoxy]-N,N-dimethyl-, (Z)-, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman-4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl]phenoxy]ethyl] and other compounds as disclosed in U.S. Pat. No. 4,839,155; 6-(4-hydroxy-phenyl)-5-[4-(2-piperidin-1-yl-ethoxy)-benzyl]-naphthalen-2-ol and other compounds as disclosed in U.S. Pat. No. 5,484,795; and {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone, GW 5638, GW 7604 and other compounds as disclosed in published international patent application WO 95/10513.

Further preferred estrogen agonists/antagonists include EM-652 (as shown in formula (III) and EM-800 (as shown in formula (IV)). The synthesis of EM-652 and EM-800 and the activity of various enantiomers is described in Gauthier et al., *J. Med. Chem.*, 1997;40:2117–2122.

(III)

(IV)

Further preferred estrogen agonists/antagonists include TSE 424 and other compounds disclosed in U.S. Pat. Nos. 5,998,402, 5,985,910, 5,780,497, 5,880,137, and European Patent Application EP 0802183 A1 including the compounds of the formulas V and VI, below:

(V)

(VI)

wherein:

$R_{1B}$ is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including triflouromethyl ether and trichloromethyl ether.

$R_{2B}$, $R_{3B}$, $R_{4B}$, $R_{5B}$, and $R_{6B}$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including triflouromethyl ether and trichloromethyl ether, cyano, $C_1$–$C_6$ alkyl (straight chain or branched), or trifluoromethyl, with the proviso that, when $R_{1B}$ is H, $R_{2B}$ is not OH.

$X_A$ is selected from H, $C_1$–$C_6$ alkyl, cyano, nitro, triflouromethyl, and halogen;

s is 2 or 3;

$Y_A$ is selected from:

a) the moiety:

wherein $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_1$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, $C_1$–$C_4$ alkylamino, di($C_1$–$C_4$)alkylamino, —NHSO$_2$R$_{1B}$, —NHCOR$_{1B}$, —NO$_2$, and phenyl optionally substituted with 1–3 (C$_1$–C$_4$)alkyl; or e) a bicyclic heterocycle containing from 6–12 carbon atoms either bridged or fused and containing up to two heteroatoms selected from the group consisting of —O—, —NH—, —N(C$_1$–C$_4$ alkyl)-, and —S(O)$_u$—, wherein u is an integer of from 0–2, optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONHR$_{1B}$, —NH$_2$, —N=, C$_1$–C$_4$ alkylamino, di(C$_1$–C$_4$)alkylamino, —NHSO$_2$R$_{1B}$, —NHCOR$_{1B}$, —NO$_2$, and phenyl optionally substituted with 1–3 (C$_1$–C$_4$) alkyl; and optical or geometric isomers thereof; and nontoxic pharmacologically acceptable acid addition salts, N-oxides, esters, quaternary ammonium salts, and prodrugs thereof.

The more preferred compounds of this invention are those having the general structures V or VI, above, wherein:

R$_{1B}$ is selected from H, OH or the C$_1$–C$_{12}$ esters or alkyl ethers thereof, and halogen;

R$_{2B}$, R$_{3B}$, R$_{4B}$, R$_{5B}$, and R$_{6B}$ are independently selected from H, OH or the C$_1$–C$_{12}$ esters or alkyl ethers thereof, halogen, cyano, C$_1$–C$_6$ alkyl, or trihalomethyl, preferably trifluoromethyl, with the proviso that, when R$_{1B}$ is H, R$_{2B}$ is not OH;

X$_A$ is selected from H, C$_1$–C$_6$ alkyl, cyano, nitro, triflouromethyl, and halogen;

Y$_A$ is the moiety:

R$_{7B}$ and R$_{8B}$ are selected independently from H, C$_1$–C$_6$ alkyl, or combined by —(CH$_2$)$_w$—, wherein w is an integer of from 2 to 6, so as to form a ring, the ring being optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_2$, C$_1$–C$_4$ alkylamino, C$_1$–C$_4$ dialkylamino, —NHSO$_2$(C$_1$–C$_4$), —HCO (C$_1$–C$_4$), and —NO$_2$; and optical and geometric isomers thereof; and nontoxic pharmacologically acceptable acid addition salts, N-oxides, esters, quaternary ammonium salts, and prodrugs thereof.

The rings formed by a concatenated R$_{7B}$ and R$_{8B}$, mentioned above, may include, but are not limited to, aziridine, azetidine, pyrrolidine, piperidine, hexamethyleneamine or heptamethyleneamine rings.

The most preferred compounds of structural formulas V and VI, above, are those wherein R$_{1B}$ is OH; R$_{2B}$–R$_{6B}$ are as defined above; X$_A$ is selected from the group of Cl, NO$_2$, CN, CF$_3$, or CH$_3$; Y$_A$ is the moiety and R$_{7B}$ and R$_{8B}$ are concatenated together as —(CH$_2$)$_t$—, wherein t is an integer of from 4 to 6, to form a ring optionally substituted by up to three subsituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$) alkyl, —NH$_2$, C$_1$–C$_4$ alkylamino, di(C$_1$–C$_4$)alkylamino, —NHSO$_2$(C$_1$–C$_4$)alkyl, —NHCO(C$_1$–C$_4$)alkyl, and —NO$_2$; and optical and geometric isomers thereof; and nontoxic pharmacologically acceptable acid addition salts, N-oxides, esters, quaternary ammonium salts, and prodrugs thereof including the compound, TSE-424, of formula (Va) below:

(Va)

The pharmaceutically acceptable acid addition salts of the estrogen agonists/antagonists of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid.

The estrogen agonists/antagonists of this invention, as discussed above, can be administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. It will also be recognized that it is possible to administer amorphous forms of the estrogen agonists/antagonists and statins.

The other active component of the combinations of this invention is a statin. The term "statin", where used in the description and the appendant claims, is synonymous with the terms "3-hydroxy-3-methylglutaryl-Coenzyme A reductase inhibitor" and "HMG-CoA reductase inhibitor." These three terms are used interchangeably throughout the description and appendant claims. As the synonyms suggest, statins are inhibitors of 3-hydroxy-3-methylglutaryl-Coenzyme A reductase and as such are effective in lowering the level of blood plasma cholesterol and promoting bone formation. Statins and pharmaceutically acceptable salts thereof are particularly useful in preventing bone loss and/or promoting bone formation and in lowering low density lipoprotein cholesterol (LDL-C) levels in mammals and particularly in humans.

The statins suitable for use herein include, but are not limited to, simvastatin, pravastatin, cerivastatin, mevastatin, fluindostatin, velostatin, fluvastatin, dalvastatin, dihydrocompactin, compactin, lovastatin, atorvastatin, bervastatin, NK-104 and ZD-4522 and pharmaceutically acceptable salts thereof.

The statins disclosed herein are prepared by methods well known to those skilled in the art. Specifically, simvastatin may be prepared according to the method disclosed in U.S. Pat. No. 4,444,784. Pravastatin may be prepared according to the method disclosed in U.S. Pat. No. 4,346,227. Cerivastatin may be prepared according to the method disclosed in U.S. Pat. No. 5,502,199. Cerivastatin may alternatively be prepared according to the method disclosed in European Patent Application Publication No. EP617019. Mevastatin may be prepared according to the method disclosed in U.S. Pat. No. 3,983,140. Velostatin may be prepared according to the methods disclosed in U.S. Pat. No. 4,448,784 and U.S. Pat. No. 4,450,171. Fluvastatin may be prepared according to the method disclosed in U.S. Pat. No. 4,739,073. Compactin may be prepared according to the method disclosed in U.S. Pat. No. 4,804,770. Lovastatin may be prepared according to the method disclosed in U.S. Pat. No. 4,231,938. Dalvastatin may be prepared according to the method disclosed in European Patent Application Publication No. EP738510. Fluvastatin may be prepared according to the method disclosed in European Patent Application Publication No. EP363934. Dihydrocompactin may be prepared according to the method disclosed in U.S. Pat. No. 4,450,171. Atorvastatin may be prepared according to the methods disclosed in U.S. Pat. No. 4,681,893 and U.S. Pat. No. 5,273,995. Bervastatin, as shown in formula VII below, may be prepared according to the methods disclosed in U.S. Pat. No. 5,082,859. NK-104, as shown in formula VII below, may be prepared by the methods disclosed in U.S. Pat. No. 5,102,888. ZD-4522, shown in formula IX below, may be prepared by the methods disclosed in U.S. Pat. No. 5,260,440.

It will be recognized that certain of the above statins contain either a free carboxylic acid or a free amine group as part of the chemical structure. Further, certain statins within the scope of this invention contain lactone moieties, which exist in equilibrium with the free carboxylic acid form. These lactones can be maintained as carboxylates by preparing pharmaceutically acceptable salts of the lactone. Thus, this invention includes pharmaceutically acceptable salts of those carboxylic acids or amine groups. The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g. sodium and potassium), alkaline earth metal salts (e.g.

calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. It will also be recognized that it is possible to administer amorphous forms of the statins.

The pharmaceutically-acceptable cationic salts of statins containing free carboxylic acids may be readily prepared by reacting the free acid form of the statin with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The pharmaceutically acceptable acid addition salts of statins containing free amine groups may be readily prepared by reacting the free base form of the statin with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

One of ordinary skill in the art will recognize that certain estrogen agonist/antagonists and statins of this invention will contain one or more atoms which may be in a particular stereochemical, tautomeric, or geometric configuration, giving rise to stereoisomers, tautomers and regio and configurational isomers. All such isomers and mixtures thereof are included in this invention. Hydrates and solvates of the compounds of this invention are also included.

The subject invention also includes isotopically-labeled estrogen agonists/antagonists and statins, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$ $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Pharmaceutical chemists will easily recognize that physiologically active compounds which have accessible hydroxy groups are frequently administered in the form of pharmaceutically acceptable esters. The literature concerning such compounds, such as estradiol, provides a great number of instances of such esters. The compounds of this invention are no exception in this respect, and can be effectively administered as an ester, formed on the hydroxy groups, just as one skilled in pharmaceutical chemistry would expect. It is possible, as has long been known in pharmaceutical chemistry, to adjust the rate or duration of action of the compound by appropriate choices of ester groups.

Certain ester groups are preferred as constituents of the compounds of this invention. The statins and/or compounds of formula I, IA, II, III, IV, V, Va, VI, VII, VIII or IX may contain ester groups at various positions as defined herein above, where these groups are represented as —COOR$^9$, R$^9$ is $C_1$–$C_{14}$ alkyl, $C_1$–$C_3$ chloroalkyl, $C_1$–$C_3$ fluoroalkyl, $C_5$–$C_7$ cycloalkyl, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl.

As used herein, the term "effective amount" means an amount of compound of the compositions, kits and methods of the present invention that is capable of treating the symptoms of the described pathological conditions. The specific dose of a compound administered according to this invention will, of course, be determined by the particular circumstances surrounding the case including, for example, the compound administered, the route of administration, the state of being of the patient, and the severity of the pathological condition being treated.

The dose of a compound of this invention to be administered to a subject is rather widely variable and subject to the judgement of the attending physician. It should be noted that it may be necessary to adjust the dose of a compound when it is administered in the form of a salt, such as a laureate, the salt forming moiety of which has an appreciable molecular weight.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject and the presence of diseases, e.g., diabetes, in the subject. All doses set forth herein, and in the appendant claims, are daily doses of the free base form of the estrogen agonists/antagonists or statins. Calculation of the dosage amount for other forms of the free base form such as salts or hydrates is easily accomplished by performing a simple ratio relative to the molecular weights of the species involved.

In general, in accordance with this invention, some of the representative statins are administered in the following dosage amounts:

simvastatin, generally about 2.5 mg to about 160 mg and preferably about 10 mg to about 40 mg;

pravastatin, generally about 2.5 mg to about 160 mg and preferably about 10 mg to about 40 mg;

cerivastatin, generally about 25 μg to about 5 mg and preferably about 1 mg to about 3.2 mg;

fluvastatin, generally about 2.5 mg to about 160 mg and preferably about 20 mg to about 80 mg;

lovastatin, generally about 2.5 mg to about 160 mg and preferably about 10 mg to about 80 mg; and atorvastatin, generally about 2.5 mg to about 160 mg and preferably about 10 mg to about 80 mg.

The general range of effective administration rates of the estrogen agonists/antagonists is from about 0.001 mg/day to about 200 mg/day. A preferred rate range is from about 0.010 mg/day to 100 mg/day. Of course, it is often practical to administer the daily dose of compound in portions, at various hours of the day. However, in any given case, the amount of compound administered will depend on such factors as the potency of the specific estrogen agonist/antagonist, the solubility of the active component, the formulation used and the route of administration.

In general, the pharmaceutical compositions will include an estrogen agonist/antagonist as a first active ingredient and a statin as a second active ingredient in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, lubricants, fillers, stabilizers, etc. Methods of formulation are well known in the art and are disclosed, for example, in *Remington's Pharmaceutical Sciences*, Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

The active ingredient compounds may be administered orally for reasons of convenience. However, the compounds may be equally effectively administered percutaneously, locally at the site of injury or as suppositories for absorption by the rectum or vagina, if desired in a given instance. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Capsules are prepared by mixing the compound or compounds with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound or compounds. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound or compounds. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavorant and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long acting by dissolving or suspending the compound or compounds in oily or emulsified vehicles which allow dispersion slowly in the serum.

The combinations of this invention may be administered in a controlled release formulation such as a slow release or a fast release formulation. Such controlled release formulations of the combination of this invention may be prepared using methods well known to those skilled in the art. The method of administration will be determined by the attendant physician or other person skilled in the art after an evaluation of the subject's condition and requirements.

The term "prodrug" means compounds that are transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A. C. S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the present invention comprises an alcohol functional group, a prodrug can be formed by the replacement of the hydrogen atom of the alcohol group with a group such as $(C_1-C_6)$alkanoyloxymethyl, 1-($(C_1-C_6)$alkanoyloxy)ethyl, 1-methyl-1-($(C_1-C_6)$ alkanoyloxy)ethyl, $(C_1-C_6)$alkoxycarbonyloxymethyl, N-$(C_1-C_6)$alkoxycarbonylaminomethyl, succinoyl, $(C_1-C_6)$ alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $-P(O)(O(C_1-C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^XO$-carbonyl, $NR^XR^{X'}$-carbonyl where $R^X$ and $R^{X'}$ are each independently $((C_1-C_{10})$alkyl, $(C_3-C_7)$cycloalkyl, benzyl, or $R^X$-carbonyl is a natural α-aminoacyl or natural α-aminoacyl-natural α-aminoacyl, $-C(OH)C(O)OY^X$ wherein ($Y^X$ is H, $(C_1-C_6)$ alkyl or benzyl), $-C(OY^{X0}) Y^{X1}$ wherein $Y^{X0}$ is $(C_1-C_4)$ alkyl and $Y^{X1}$ is $((C_1-C_6)$alkyl, carboxy$(C_1-C_6)$alkyl, amino $(C_1-C_4)$alkyl or mono-N— or di-N,N-$(C_1-C_6)$ alkylaminoalkyl, $-C(Y^{X2}) Y^{X3}$ wherein $Y^{X2}$ is H or methyl and $Y^{X3}$ is mono-N— or di-N,N-$(C_1-C_6)$alkylamino, morpholino, piperidin-1-yl or pyrrolidin-1-yl.

Advantageously, the present invention also provides kits for use by a consumer to promote bone formation and/or prevent bone loss and lower blood cholesterol, including treating subjects suffering from cardiovascular disease, atherosclerosis and hyperlipidemia and treating subjects presenting with symptoms of cardiac risk. The kits comprise a) a pharmaceutical composition comprising an estrogen agonist/antagonist and a pharmaceutically acceptable carrier, vehicle or diluent; b) a pharmaceutical composition comprising a statin and a pharmaceutically acceptable carrier, vehicle or diluent; and, optionally, c) instructions describing a method of using the pharmaceutical compositions to promote bone formation and/or prevent bone loss and lower blood cholesterol. The instructions may also indicate that the kit is to promote bone formation and/or prevent bone loss and lower blood cholesterol while substantially reducing the concomitant liability of adverse effects associated with estrogen administration. The estrogen agonist/antagonist and the statin contained in the kit may be optionally combined in the same pharmaceutical composition.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday,". . . etc . . . "Second Week, Monday, Tuesday, . . . " etc. Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Based on a reading of the present description and claims, certain modifications to the compositions and methods described herein will be apparent to one of ordinary skill in the art. The claims appended hereto are intended to encompass these modifications.

All references and patents cited herein are incorporated by reference.

EXAMPLES

Example 1

Estrogen Receptor Binding

Estrogen and estrogen agonist/antagonist binding affinity was measured by the following protocol:

cDNA cloning of human ERα: The coding region of human ERα was cloned by RT-PCR from human breast cancer cell mRNA using Expand™ High Fidelity PCR System according to manufacturer's instructions (Boehringer-Mannheim, Indianapolis, Ind.). PCR products were cloned into pCR2.1 TA Cloning Kit (Invitrogen, Carlsbad, Calif.) and sequenced. Each receptor-coding region was subcloned into the mammalian expression vector pcDNA3 ((Invitrogen, Carlsbad, Calif.).

Mammalian cell expression. Receptor proteins were overexpressed in 293T cells. These cells, derived from HEK293 cells (ATCC, Manassas, Va.), have been engineered to stably express large T antigen and can therefore replicate plasmids containing a SV40 origin of replication to high copy numbers. 293T cells were transfected with either hERα-pcDNA3 or hERβ-pcDNA3 using lipofectamine as described by the manufacturer (Gibco/BRL, Bethesda, Md.). Cells were harvested in phosphate buffered saline (PBS) with 0.5 mM EDTA at 48 h post-transfection. Cell pellets were washed once with PBS/EDTA. Whole cell lysates were prepared by homogenization in TEG buffer (50 mM Tris pH 7.4, 1.5 mM EDTA, 50 mM NaCl, 10% glycerol, 5 mM DTT, 5 μg/ml aprotinin, 10 μg/ml leupeptin, 0.1 mg/ml Pefabloc) using a dounce homogenizor. Extracts were centrifuged at 100,000×g for 2 h at 4° C. and supernatants were collected. Total protein concentrations were determined using BioRad reagent (BioRad, Hercules, Calif.).

Competition binding assay. The ability of various compounds to inhibit [$^3$H]-estradiol binding was measured by a competition binding assay using dextran-coated charcoal as has been described (Leake R E, Habib F 1987 Steroid hormone receptors: assay and characterization. In: B. Green and R. E. Leake (eds). Steroid Hormones a Practical Approach. IRL Press Ltd, Oxford. 67–92.) 293T cell extracts expressing either hERα or hERβ were incubated in the presence of increasing concentrations of compound to be tested and a fixed concentration of [$^3$H]-estradiol (141 μCi/mmol, New England Nuclear, Boston, Mass.) in 50 mM Tris HCl pH 7.4, 1.5 mM EDTA, 50 mM NaCl, 10% glycerol, 5 mM DTT, 0.5 mg/mL β-lactoglobulin in a final volume of 0.2 mL. All compounds to be tested were dissolved in dimethylsulfoxide. The final concentration of receptor was 50 pM with 0.5 nM [$^3$H]-estradiol. After 16 h at 4° C., dextran-coated charcoal (20 μL) was added. After 15 min at room temperature the charcoal was removed by centrifugation and the radioactive ligand present in the supernatant was measured by scintillation counting. All reagents were obtained from Sigma (St. Louis, Mo.) unless otherwise indicated.

Figure 1:
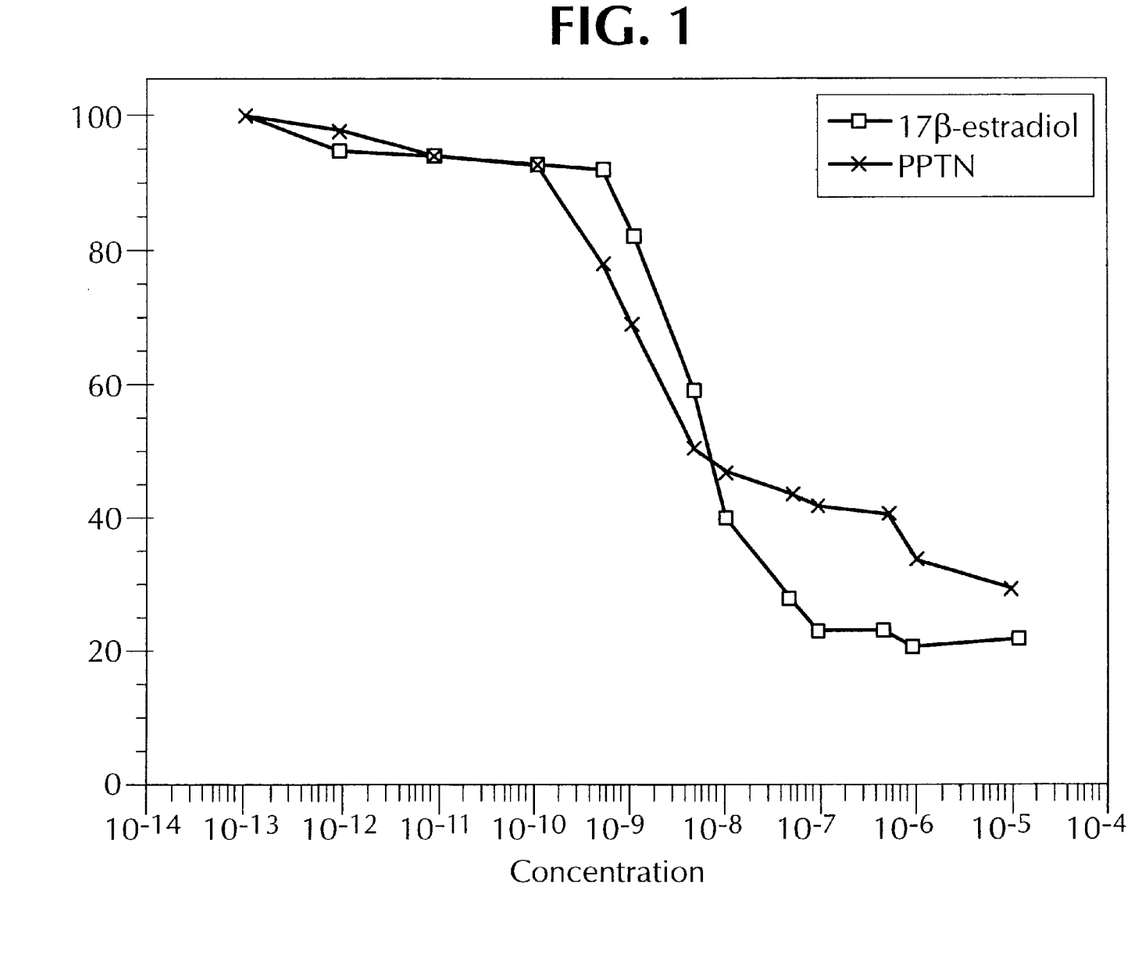
FIG. 1 is a log-linear competition binding plot of PPTN and 17β-estradiol to human estrogen receptor. The X-axis represents percentage of radiolabeled estrogen bound to receptor. The Y-axis represents molar concentration of added ligand. Values are mean ±SEM.

The binding affinity of (−)-cis-6-phenyl-5-[4-(2-pyrrolidin-1-yl-ethoxy)-phenyl]-5,6,7,8-tetrahydro-naphthalene-2-ol (PPTN) and 17β-estradiol were measured using recombinant human estrogen receptor (ER). FIG. 1 shows the results of the binding experiment in which the binding of PPTN was found to be similar to that of 17β-estradiol.

Example 2

Inhibition of in vitro Human Breast Tumor Cell Growth

The in vitro antiproliferative effects of (−)-cis-6-phenyl-5-[4-(2-pyrrolidin-1-yl-ethoxy)-phenyl]-5,6,7,8-tetrahydro-naphthalene-2-ol (PPTN) were tested using two types of human breast cancer cell lines: first, MCF-7 cells, which contain ER as well as progesterone receptors (PgR), and second, MDA-MB-231 cells, which lack ER and PgR, and enable the determination of an effect that is independent of the ER mechanism. The effect of PPTN on the growth of these different cell lines was determined by incubation of the cells with various compound concentrations for 6 days.

The antiproliferative effects were then determined by direct cell counts. PPTN inhibited the growth of the ER-positive cell line MCF-7. The $IC_{50}$ for growth inhibition was approximately 3 to $5 \times 10^{-11}$ M. In MDA-MB-231, ER-negative cell lines, the compound did not inhibit cell proliferation. These results indicate that growth inhibition was ER-specific and not due to cytotoxicity since the compound had no measurable effect on the ER-negative cell line.

Example 3

Effect of (−)-Cis-6-phenyl-5-[4-(2-pyrrolidin-1-yl-ethoxy)-phenyl]-5,6,7,8-tetrahydro-naphthalene-2-ol (PPTN) in the Ovariectomized Rat Model: A Model of Post-Menopausal Osteoporosis In women, estrogen deficiency during the menopause results in increased bone turnover leading to bone loss. Ovariectomy in rats produces estrogen deficiency and increased bone turnover leading to trabecular bone loss similar to that observed in post-menopausal women (Kalu, D. N., *Bone and Mineral* 1991;15:175; Frost, H. M., Jee W. S. S., *Bone and Mineral* 1992;18:227; Wronski, T. J., Yen, C-F, *Cells Materials* 1991;(suppl. 1):69). The OVX rat is thus an appropriate model to evaluate compounds for the prevention and treatment of post-menopausal osteoporosis. The ability of PPTN to inhibit estrogen deficiency bone loss was assessed in 5-month-old OVX rats, since ovariectomy causes significant bone loss in the lumbar vertebrae, proximal tibia, and distal femoral metaphyses (Ke, H. Z., et al., *Endocrin* 1995;136:2435; Chen, H. K., et al., *J Bone Miner Res* 1995;10:1256).

Five-month-old OVX female rats were treated with PPTN at oral doses of 0.733, 7.33, 73.3, and 733 μg/kg/day, or 17α-ethynyl estradiol (EE) at 30 μg/kg/day (10 rats per subgroup) daily for 4 weeks. The oral treatment began 1 day after surgery. Groups of vehicle-treated sham rats (n=10) and vehicle-treated OVX rats (n=10) served as controls. Calcein at 10 mg/kg was injected s.c. to all rats 12 and 2 days before necropsy as a fluorochrome bone marker to measure bone dynamic histomorphometric parameters. The effects of PPTN on the following end points were determined: (a) serum osteocalcin, a biochemical marker of bone turnover, (b) bone mineral density of lumbar vertebrae and distal femoral metaphyses, (c) bone histomorphometry of fifth lumbar vertebral body and proximal tibial metaphyses.

Serum osteocalcin concentration was determined by radioimmunoassay. Four weeks after surgery, serum osteocalcin concentration increased significantly by 85% in vehicle-treated OVX controls, compared with vehicle-treated sham controls. This increase was completely prevented by treatment with PPTN at doses ≧7.33 μg/kg/day, or by treatment with EE. Therefore, both 7.33 μg/kg/day of PPTN and EE prevented the increase in osteocalcin concentration induced by estrogen deficiency in rats. These data suggest that PPTN inhibits bone turnover induced by estrogen deficiency.

The first to the sixth lumbar vertebrae from each rat were removed during necropsy. These were then scanned ex vivo using dual-energy X-ray absorptiometry. The scan images were analyzed, and bone area, bone mineral content (BMC), and bone mineral density (BMD) of whole lumbar vertebrae (WLV), and LV1 through LV6 were determined. Bone areas of WLV, and LV1 through LV6 did not differ between groups. The changes in BMC were similar to those observed in BMD. Further, the changes in BMD of WLV were identical to those observed in each of six vertebrae. Therefore, only the changes in the whole lumbar vertebrae are reported.

Following ovariectomy with vehicle treatment, a significant decrease in BMD of lumbar vertebrae was found at 4 weeks after ovariectomy. PPTN at all dose levels and EE completely prevented the decrease in lumbar vertebral BMD. Furthermore, BMD in OVX rats treated with 73.3 μg/kg/day of PPTN increased significantly as compared with both sham and OVX controls. These data indicate that PPTN at doses as low as 0.733 μg/kg/day completely prevented lumbar vertebral bone loss induced by estrogen deficiency.

In order to understand the cellular mechanism of bone-protective effects of PPTN at the tissue level, bone histomorphometric methods were used to determine the effects of PPTN on cancellous bone of the fifth lumbar vertebral body in OVX rats. Ovariectomy caused significant decreases in trabecular bone volume (trabecular bone area divided by marrow space area, expressed as percent) and trabecular number, and a significant increase in trabecular separation of the fifth lumbar vertebral body. These changes induced by ovariectomy were completely prevented by treatment with all doses of PPTN and EE. Further, trabecular number was significantly increased in OVX rats treated with EE or PPTN at 73.3 or 733 μg/kg/day as compared with sham controls. These data revealed that PPTN is a bone protective agent in estrogen-deficient rats. The $ED_{50}$ of PPTN in preserving lumbar vertebral cancellous bone mass and structure in OVX rats was less than 0.733 μg/kg/day.

A significant increase in percent eroded surface (+59%), an index of osteoclastic bone resorption, was found in vehicle-treated OVX rats compared with vehicle-treated sham controls. Similar to EE, PPTN at all dose levels significantly decreased percent eroded surface in OVX rats compared with sham controls. Therefore, PPTN prevented bone loss in OVX rats by inhibiting bone resorption associated with estrogen deficiency.

Ovariectomy resulted in a significant increase in bone formation rate (BFR, amount of bone formation per unit bone surface), an index of bone turnover, while EE and PPTN at all dose levels inhibited this increase.

Bone turnover rate was significantly increased in vehicle-treated OVX rats compared with vehicle-treated sham controls. Bone turnover rate in OVX rats treated with either PPTN or EE did not differ from sham controls, indicating PPTN at all dose levels and EE completely prevented the increase in bone turnover associated with estrogen deficiency.

In summary, PPTN prevented lumbar vertebral bone loss by inhibiting bone resorption and bone turnover associated with estrogen deficiency in a manner indistinguishable from estrogen. The $ED_{50}$ of PPTN in preserving trabecular bone in this model was less than 0.733 μg/kg/day.

Using dual-energy X-ray absorptiometry, the right femur of each rat was scanned ex vivo. Bone mineral density (BMD) of the distal femoral metaphyses (second 0.5 cm from the distal end of femur) and the proximal femur (the first 0.5 cm from the proximal end of femur, which contains the femoral head, neck, and greater trochanter) was determined.

Four weeks after ovariectomy in vehicle-treated rats, BMD of distal femoral metaphyses and proximal femora significantly decreased. EE prevented the decrease in BMD of distal femoral metaphyses, but had no effect on proximal femoral BMD. In OVX rats treated with PPTN at 0.733 or 7.33 μg/kg/day, BMD of distal femoral metaphyses and proximal femur did not differ from OVX controls. However, PPTN at both 73.3 and 733 μg/kg/day completely prevented the decreases in BMD of distal femoral metaphyses and proximal femur in OVX rats.

In order to determine the effect of PPTN on long bone metaphyses, histomorphometric analyses were performed on the proximal tibiae. Trabecular bone volume significantly decreased in vehicle-treated OVX controls compared with sham controls. PPTN at doses ≧7.33 μg/kg/day had significantly greater trabecular bone volume compared with OVX controls. At 0.733 μg/kg/day, PPTN had no significant effect on trabecular bone volume. The $ED_{50}$ of PPTN in preserving proximal tibial trabecular bone mass in OVX rats was between 0.733 and 7.33 μg/kg/day.

Significant increases in indices of osteoclastic bone resorption (osteoclast number per millimeter of bone surface and percent osteoclast surface) were found in vehicle-treated OVX rats compared with vehicle-treated sham controls. Similar to EE, PPTN at 7.33, 73.3, or 733 μg/kg/day dose levels significantly decreased osteoclast number per millimeter of bone surface and percent osteoclast surface compared with both sham and OVX controls. Further, percent osteoclast surface decreased significantly in OVX rats treated with PPTN at 0.733 μg/kg/day compared with OVX controls.

Ovariectomy significantly increased the bone turnover rate in proximal tibial trabecular bone compared with vehicle-treated sham controls. The bone turnover rate in OVX rats treated with either PPTN or EE did not differ from sham controls with the exception of PPTN at the 0.733 μg/kg/day dose, indicating that PPTN at doses of 7.33 to 733 μg/kg/day prevented the increase in bone turnover associated with estrogen deficiency and maintained it at sham control levels.

In summary, PPTN had similar effects in preserving bone mineral density and trabecular bone volume in both proximal tibiae and lumbar vertebrae. The discrepancy between lumbar vertebrae and proximal tibiae in response to PPTN administration was found only at 0.733 μg/kg/day, which indicated that PPTN at 0.733 μg/kg/day completely prevented bone loss in lumbar vertebrae and failed to do so in proximal tibiae. Therefore, the $ED_{50}$ of PPTN in preserving cancellous bone mass and inhibiting bone resorption was less than 0.733 μg/kg/day in lumbar vertebrae, and between 0.733 and 7.33 μg/kg/day in proximal tibiae.

Example 4

Reduction of Cholesterol Levels of 0.2% Cholesterol-Fed New-Zealand White Rabbits New Zealand White rabbits (female, aged 3–4 months, weighing less than 3 Kg), six in each group, are fed a control diet of 0.2% cholesterol (100 g rabbit chow daily containing 0.2 g cholesterol) or a diet of 0.2% cholesterol and a pharmaceutical composition containing an estrogen agonist/antagonist or a diet of 0.2% cholesterol and a pharmaceutical composition containing a statin or a diet of 0.2% cholesterol and a pharmaceutical composition containing an estrogen agonist/antagonist and a statin at a dose equivalent to the doses of the estrogen agonist/antagonist and statin administered to the groups receiving diet containing only estrogen agonist/antagonist and only statin. After 56 days, plasma or serum is collected from the rabbits and cholesterol levels are determined using the enzymatic method of Mao, et al., Clin. Chem. (1983) 29: 1890–1897.

What is claimed is:

1. A method of promoting bone formation, the method comprising: co-administering to a subject in need thereof an effective amount of (−)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof and atorvastatin calcium.

2. The method of claim 1 wherein the (−)-cis-6-phenyl-5-[4-(2-pyrrolidin-1-yl-ethoxy)-phenyl]-5,6,7,8-tetrahydro-naphthalene-2-ol is in the form of the D-tartrate salt.

3. A method of preventing bone loss, the method comprising: co-administering to a subject in need thereof an effective amount of (−)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof and atorvastatin calcium.

4. The method of claim 3 wherein the (−)-cis-6-phenyl-5-[4-(2-pyrrolidin-1-yl-ethoxy)-phenyl]-5,6,7,8-tetrahydro-naphthalene-2-ol is in the form of the D-tartrate salt.

5. A method of treating osteoporosis, the method comprising: co-administering to a subject in need thereof an effective amount of (−)-cis-6-phenyl-5-[4-(2-pyrrolidin-1-yl-ethoxy)-phenyl)-5,6,7,8-tetrahydro-naphthalene-2-ol or an optical or geometric isomer thereof; a pharmaceutically acceptable salt, N-oxide, ester, quaternary ammonium salt, or a prodrug thereof and atorvastatin calcium.

6. The method of claim 5 wherein the (−)-cis-6-phenyl-5-[4-(2-pyrrolidin-1-yl-ethoxy)-phenyl]-5,6,7,8-tetrahydro-naphthalene-2-ol is in the form of the D-tartrate salt.

* * * * *